(12) United States Patent
Runnebaum et al.

(10) Patent No.: US 9,790,143 B2
(45) Date of Patent: Oct. 17, 2017

(54) DELAMINATED ZEOLITE CATALYZED AROMATIC ALKYLATION

(71) Applicants: Ron C. Runnebaum, Sacramento, CA (US); Xiaoying Ouyang, El Cerrito, CA (US); Alexander S. Katz, Richmond, CA (US); Stacey Ian Zones, San Francisco, CA (US)

(72) Inventors: Ron C. Runnebaum, Sacramento, CA (US); Xiaoying Ouyang, El Cerrito, CA (US); Alexander S. Katz, Richmond, CA (US); Stacey Ian Zones, San Francisco, CA (US)

(73) Assignees: The Regents of the University of California, Oakland, CA (US); Chevron U.S.A. Inc., San Ramon, CA (US)

( * ) Notice: Subject to any disclaimer, the term of this patent is extended or adjusted under 35 U.S.C. 154(b) by 112 days.

(21) Appl. No.: 14/530,337

(22) Filed: Oct. 31, 2014

(65) Prior Publication Data
US 2015/0126789 A1    May 7, 2015

(51) Int. Cl.
*C07C 2/66*    (2006.01)
*C07C 2/64*    (2006.01)
*C07C 2/86*    (2006.01)

(52) U.S. Cl.
CPC ............... *C07C 2/66* (2013.01); *C07C 2/864* (2013.01); *C07C 2529/06* (2013.01); *C07C 2529/70* (2013.01)

(58) Field of Classification Search
None
See application file for complete search history.

(56) References Cited

U.S. PATENT DOCUMENTS

| 5,087,784 | A | * | 2/1992 | Primack | .................. | B01J 8/003 |
| | | | | | | 203/DIG. 6 |
| 5,324,877 | A | | 6/1994 | West et al. | | |
| 6,855,855 | B2 | | 2/2005 | Van Den Brink et al. | | |
| 2004/0138051 | A1 | | 7/2004 | Shan et al. | | |

(Continued)

FOREIGN PATENT DOCUMENTS

| EP | 1068898 B1 | 12/2004 |
| WO | 01/21562 A1 | 3/2001 |
| WO | 2012/175601 A1 | 12/2012 |

OTHER PUBLICATIONS

Schreyeck et al., Prefer: a new layered (alumino) silicate precursor of FER-type zeolite, Microporous Materials, vol. 6, Jul. 1996, pp. 259-271.*

(Continued)

*Primary Examiner* — Philip Louie
(74) *Attorney, Agent, or Firm* — E. Joseph Gess; Melissa M. Hayworth (57) ABSTRACT

Provided is a method of alkylating an aromatic compound comprising contacting an aromatic compound and an alkylating agent in the presence of UCB-3 as a catalyst under reaction conditions suitable for aromatic alkylation. The aromatic compound preferably comprises benzene or toluene and the alkylation agent preferably comprises an olefin or alcohol. Lower temperature ranges can be used for the reaction, for example in the range of from 100 to 300° C.

16 Claims, 7 Drawing Sheets

(56) References Cited

U.S. PATENT DOCUMENTS

2006/0138025 A1* 6/2006 Zones .................. B01J 29/86
208/111.01
2012/0148487 A1 6/2012 Katz et al.

OTHER PUBLICATIONS

International Search Report from corresponding PCT Application PCT/US2014/063551 mailed on Feb. 24, 2015.
Corma, A., "Inorganic Solid Acids and Their Use in Acid-Catalyzed Hydrocarbon Reactions", Chem. Rev., vol. 95 (1995); 559-614.
Gounder R. and Iglesia, E., "The Roles of Entropy and Enthalpy in Stabilizing Ion-Pairs at Transition States in Zeolite Acid Catalysis", Acc. Chem. Res., vol. 45, No. 2 (2011); 229-238.
Matias, P., et al., "Methylcyclohexane transformation over HMCM22 zeolite: Mechanism and location of the reactions", J. Catal., vol. 259 (2008);190-202.
Corma, A. et al. "Alkylation of Benzene with Short-Chain Olefins over MCM-22 Zeolite: Catalytic Behaviour and Kinetic Mechanism", J. Catal., vol. 192 (2000);163-173.
Corma, A. et al. "Characterization and Catalytic Activity of MCM-22 and MCM-56 Compared with ITQ-2", J. Catal., vol. 191 (2000); 218-224.
Corma, A. et al., "Delaminated Zeolites: Combining the Benefits of Zeolites and Mesoporous Materials for Catalytic Uses", J. Catal., vol. 186 (1999); 57-63.
Corma, A. et al. "Delaminated zeolite precursors as selective acidic catalysts", Nature, vol. 396 (1998); 353-356.
Gounder R. and Iglesia, E. "The catalytic diversity of zeolites: confinement and solvation effects within voids of molecular dimensions", Chem. Commun., vol. 49 (2013); 3491-3509.
Degnan, T.F. Jr. et al. "Alkylation of aromatics with ethylene and proplyene: recent developments in commercial processes", Appl. Catal. A., vol. 221 (2001); 283-294.
Rigoreau, J. et al. "Alkylation of touene with propene over H-MCM-22 zeolite. Location of the main and secondary reactions", J. Catal., vol. 236 (2005); 45-54.

* cited by examiner

DELAMINATED ZEOLITE CATALYZED AROMATIC ALKYLATION

RELATED APPLICATION

This application claims priority to U.S. Provisional Application Ser. No. 61/899,084, entitled "Delaminated Zeolite Catalyst Aromatic Alkylation", filed 1 Nov. 2013, the entire contents of which is incorporated herein by reference in its entirety.

BACKGROUND OF THE INVENTION

Field of the Invention

The present invention relates to a process of aromatic alkylation. More specifically, provided is a process of aromatic alkylation catalyzed by delaminated zeolites exhibiting improved reaction rates.

Description of the Related Art

Figure 1A:
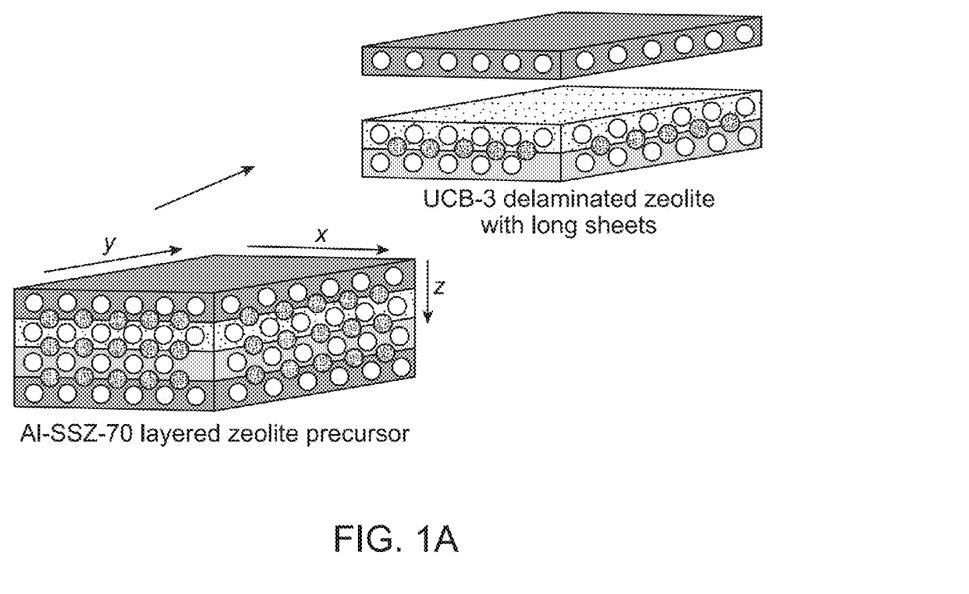
FIGS. 1A and 1B show schematic representations of delamination decreasing the characteristic diffusion-path length of the microporous channels by breaking zeolite sheets into smaller fragments. Two possible benefits of Al-SSZ-70 delamination are shown in FIGS. 1A and 1B.

Zeolites demonstrate extraordinary catalytic utility due to their well-defined catalytic active sites consisting of heteroatoms substituted within the zeolitic framework as well as shape selectivities. The crystallinity of zeolites enables high densities of uniform and well-defined acid sites, which are impossible to achieve with amorphous silica-alumina materials, and are useful as solid-acid catalysts for a number of reaction classes, including isomerization, dehydration, and alkylation. See, Corma, A. *Chem. Rev.* 1995, 95, 559-614; see Degnan Jr., T. F.; Smith, C. M.; Venkat, C. R. *Appl. Catal., A* 2001, 221, 283-294. Though sometimes all of the microporous surface area of the zeolite is available for catalysis (isomerization of 1-hexene, or alkylation of benzene with methanol to form p-xylene), in many other instances the sterics of the zeolite framework severely limits where catalysis can occur. See Gounder, R.; Iglesia, E. *Acc. Chem. Res.* 2011, 45, 229-238; see Gounder, R.; Iglesia, E. *Chem. Commun.* 2013, 49, 3491-3509; see Matias, P.; Lopes, J. M.; Laforge, S.; Magnoux, P.; Russo, P. A.; Ribeiro Carrott, M. M. L.; Guisnet, M.; Ramôa Ribeiro, F. J. *Catal.* 2008, 259, 190-202. Such is the case in aromatic alkylation with $C_3$ and larger olefins, when using MWW-type zeolites such as MCM-22, which are industrial solid-acid catalysts for aromatic alkylation. Only a small fraction of the total number of acid sites is typically invoked as being active under reaction conditions in this case—those located on the external surface. See, Corma, A.; Martínez-Soria, V.; Schnoeveld, E. J. *Catal.* 2000, 192, 163-173; see, Millini, R. In *Zeolites and Ordered Porous Solids: Fundamentals and Applications* 2011; and see, Rigoreau, J.; Laforge, S.; Gnep, N. S.; Guisnet, M. J. *Catal.* 2005, 236, 45-54. Delamination of MWW-type layered zeolite precursors aims to synthesize catalysts with increased density of external acid sites. This leads to higher reaction rates and less deactivation for aromatic alkylation reactions. See, Corma, A.; Diaz, U.; Fornés, V.; Guil, J. M.; Martínez-Triguero, J.; Creyghton, E. J. *J. Catal.* 2000, 191, 218-224; see, Corma, A.; Fornés, V.; Martínez-Triguero, J.; Pergher, S. B. *J. Catal.* 1999, 186, 57-63; see, Corma, A.; Fornes, V.; Pergher, S. B.; Maesen, T. L. M.; Buglass, J. G. *Nature* 1998, 396, 353-356; and see Van Den Brink, P. J.; Corma, A.; Creyghton, E. J.; Fornés, V.; Martinez, V. Aromatics Alkylation. U.S. Pat. No. 6,855,855, Feb. 15, 2005. This has been presumed to arise from the increased external surface area of the delaminated material, as shown in FIG. 1A. In a MWW-type layered material, delamination occurs parallel to the two non-intersecting micropore channels that are used for molecular transport via diffusion, represented by the x-y plane of FIG. 1A. Because delamination is parallel to the direction of internal transport, the conventional belief has been that the benefit of delamination of MWW-type layered materials on the reaction rate is limited to only external acid-site density effects.

The industry would be well served by better understanding the catalysis of aromatic alkylation, and providing a catalytic aromatic alkylation process which has a higher reaction rate.

SUMMARY OF THE INVENTION

Provided is a method of alkylating an aromatic compound comprising contacting an aromatic compound and an alkylation agent in the presence of UCB-3 as a catalyst under reaction conditions suitable for aromatic alkylation. In one embodiment, the aromatic compound comprises toluene and the alkylating agent comprises an olefin such as propylene. In one embodiment, the temperature range for the reaction is in the range of from 100 to 300° C.

Among other factors, the present invention recognizes that use of a delaminated zeolite catalyst increases rates of reaction in the alkylation of an aromatic compound. The UCB-3 catalyst is effective due to a decrease in the characteristic diffusion-path length along internal microporous channels, due to breakage of sheets into smaller pieces in a direction perpendicular to delamination, i.e. along the x and y directions. See, for example, FIG. 1B. This in turn leads to higher rates of diffusive transport to internal acid sites. A 2-4 fold increase in reaction rate is achieved in aromatic alkylation relative to conventional catalysts used in aromatic alkylation reactions.

BRIEF DESCRIPTION OF THE DRAWINGS

FIG. 1A shows the conventional benefit consisting of separated long sheets and FIG. 1B shows a different benefit of delamination, in which UCB-3 delaminated zeolite consists of shorter sheets formed by the breakage of layers during delamination. Un-filled circles (○) indicate 10-MR openings to intralayer sinusoidal micropore channels and dotted circles (◉) indicate openings to interlayer micropore channels containing supercages.

DETAILED DESCRIPTION OF THE INVENTION

The present invention provides a new method for aromatic alkylation. The method comprises contacting an aromatic compound and an alkylating agent in the presence of UCB-3 as a catalyst under reaction conditions suitable for aromatic alkylation. The reaction can take place in a conventional reactor containing the UCB-3 catalyst in a catalyst bed. It has been discovered that the use of UCB-3 as a catalyst in aromatic alkylation can provide a 2 to 4 fold increase in reaction rate, depending on the temperature of the reaction. The lower the reaction temperature, the greater the increase in reaction rate relative to commercial catalysts for aromatic alkylation, e.g., such as Al-SSZ-70.

The aromatic-compound used in the reaction can be any suitable aromatic compound for aromatic alkylation. For example, the aromatic compound can be benzene or toluene. In one embodiment, the aromatic compound is toluene. In another embodiment the aromatic compound is benzene.

The alkylating agent used in the reaction can be any suitable alkylating agent as is known. For example, the alkylating agent can be an alkane, olefin or an alcohol. In one embodiment, the alkane is methane or ethane. In one embodiment, the olefin is ethylene or a proplylene. Propylene is used in one embodiment. In another embodiment, the alkylating agent can be an alcohol, such as methanol or isopropanol. The use of propylene as the alkylating agent with toluene as the aromatic compound in an aromatic alkylation in the presence of UCB-3 has been found quite successful in achieving a relative increase in reaction rate. In another embodiment, benzene is alkylated with either ethylene, propylene or isopropanol.

The relative increase in reaction rate increases as the reaction temperature is lowered. Particularly good results, with increases of 3 to 4 fold in reaction rate relative to a conventional catalyst, have been observed in the temperature range of 0° C. to 500° C., and in one embodiment the temperature range of 100 to 300° C. In one embodiment, the temperature of the reaction is in the range of from 150 to 250° C. In another embodiment, the temperature of the reaction is in the range of from 150 to 250° C. and is employed with pressure of 1 to 30 atm.

Overall, the reaction conditions for the aromatic alkylation reaction can be conventional conditions. For example, the reactor pressure can vary, but typically ranges from about 0.2 to 250 atm. In one embodiment, the pressure ranges from 1 to 30 atm. The reactor temperatures, as noted above, can be lower in range. This allows for a relative good reaction rate while saving energy. However, the temperature can range up to conventional 700° C. temperatures, e.g., 0° C. to 700° C. Even at higher temperatures, improvements in the reaction rates are observed, for example, at least 2 fold. Upon introduction of feed into the reactor, the catalyst bed temperature may be adjusted to a selected reaction temperature to effect a desired conversion. That temperature can be lower when using UCB-3 as the catalyst in the present invention. The temperature may be increased gradually at a rate of from about 1° C./min to about 10° C./min to provide the desired final reactor temperature.

The catalyst UCB-3 can be prepared by delamination of a layered zeolite precursor of either PREFER or an SSZ-70, i.e., either Al-SSZ-70 or B-SSZ-70. Generally, a halide anion delamination process is used, and a non-aqueous solution is used for delamination Dimethylformamide (DMF) has been found to be suitable as the organic solvent for the process. The processing discussed in U.S. Publication No. 2012/0148487, published Jun. 14, 2012, can be used successfully. U.S. Publication No. 2012/0148487 is herein incorporated by reference in its entirety.

The UCB-3 catalyst in one embodiment has a Si/Al ratio greater than 25. In one embodiment, the UCB-3 catalyst has a Si/Al ratio of about 40.

The effectiveness of UCB-3 as a catalyst in aromatic alkylation compared to a conventional catalyst such as Al-SSZ-70 is clear upon a comparison of the two. In one embodiment, UCB-3 is prepared via delamination of Al-SSZ-70 using a halide anion delamination process. The materials characterization data are summarized in Table 1 below, and demonstrate a 2-fold increase in external-surface area upon delamination, when comparing calcined UCB-3 with its three-dimensional (3D) zeolite counterpart (calcined Al-SSZ-70).

TABLE 1

Material and catalytic characterization data of calcined UCB-3, calcined Al-SSZ-70, and calcined Al-MCM-22, including external-surface area as measured by $N_2$ physisorption; total and external Brønsted acid-sites as measured by amine chemisorption; and overall reaction rate.

| Sample | Si:Al | $S_{external}$[a] $m^2/g$ | Total acid sites measured by pyridine adsorption[b] μmol/g | External acid sites measured by bulky amines | | Rate of reaction at various temperatures[d] | |
|---|---|---|---|---|---|---|---|
| | | | | collidine[b] | acridine[c] | 423 K | 523 K |
| | | | | μmol/g | | mol (g of catalyst)$^{-1}$ h$^{-1}$ | |
| Al-SSZ-70 | 40 | 100 | 299 | 135 | 140 | 0.031 | 0.082 |
| UCB-3 | 40 | 190 | 257 | 170 | 252 | 0.108 | 0.198 |
| MCM-22 | 25 | 60 | 512 | 70 | 81 | — | 0.101 |

[a]determined by t-plot method; thickness range 0.4-0.6 nm
[b]measured by TGA
[c]measured by UV-VIS
[d]rate of reaction at zero time-on-stream.

Figure 2A:
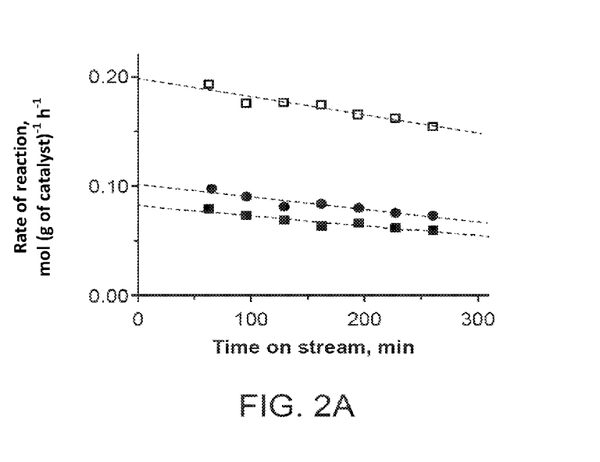
FIGS. 2A-2D show the change in toluene conversion catalyzed by UCB-3 (□), Al-SSZ-70 (■), and Al-MCM-22 (●) as a function of time-on-stream at 523 K (250° C.) (FIG. 2A) and 423 K (100° C.) (FIG. 2C). Cross-plots of the rates of product formation shown for reaction temperatures of 523 K (250° C.) (FIG. 2B) and 423 K (150° C.) (FIG. 2D) at various times-on-stream. Closed symbols characterize Al-MCM-22 versus UCB-3: m- (■), p- (♦), and o- (●) isopropyltoluene. Open symbols characterize Al-SSZ-70 versus UCB-3: m- (□), p- (◇), and o- (○) cymene. Rates are in units of mol (g of catalyst)$^{-1}$ h$^{-1}$.
Figure 2B:
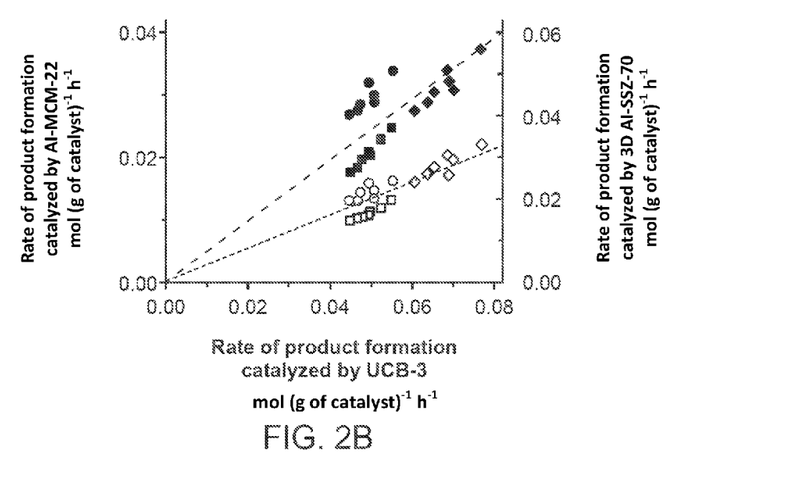

Calcined UCB-3 and 3D Al-SSZ-70 were compared as catalysts for toluene alkylation with propylene at various temperatures. Data shown in FIG. 2A represent toluene conversion versus time-on-stream for a once-through packed-bed flow reactor at 523 K) (250°). Calcined UCB-3 exhibited a 2.4-fold increase in reaction rate when extrapolated to zero time-on-stream relative to 3D Al-SSZ-70 under the same reaction conditions. This is nearly equal to the increase in external-surface area accompanying delamination, and can therefore be rationalized by the increase in external acid site density according to FIG. 1A (vide supra). The selectivity profiles of each catalyst were compared for the three major products (ortho-, meta-, and para-cymene isomers) by using cross plots in FIGS. 2A-2D, which are graphical representations of the product isomer distribution of one catalyst on one set of orthogonal axes plotted versus another catalyst on the other set of axes. A linear trend in the cross plot results from an identical product selectivity profile for the two catalysts being compared (i.e. when the absolute rates may be different by the same factor for all isomers but the relative rates of forming any two products are the same between the two catalysts being compared). This concept of using cross plots to compare selectivities of two different catalysts is similar to the concept of parity plots, which are typically used to compare experimental versus theoretical (modeling) data. When the agreement between the two is good, the points in the parity plot lie on a y=x line (see Chapter 10 in *Experimental Methods in Kinetic Studies*, Revised Edition, "Statistical Evaluation of Multiparameter Fits", Wojciechowski, B. W. and Rice, N. M., Elsevier Science B. V., Amsterdam, The Netherlands (2003)). In our case, we are not comparing the experimental versus theoretical data, but rather we are comparing the selectivity distribution of two catalysts, using a similar concept. Our phase plot consists of rates of production of three isomers for two catalysts, with data for one catalyst represented by the y axis and data for the other by the x axis. If the relative rates of production for all three isomers are different by the same constant between the two catalysts being compared, the parity plot that we are using will be linear (equation of form y=mx where m is a constant). On the other hand, if two catalysts have significantly different isomer distributions (selectivity profiles), then the parity plot that we are using will be nonlinear, and can be highly nonlinear. Thus, the linearity of the parity plot tells us directly how similar the selectivities of two catalysts being compared are. The more linear the plot (equation of form y=mx going through origin), the more similar the selectivities of the two catalysts being compared. Data in FIG. 2B demonstrate relatively high ortho and low meta selectivities for both UCB-3 and 3D Al-SSZ-70, which have also been observed in other reaction systems such as the analogous Friedel-Crafts aromatic alkylation. The linearity of these data demonstrates a lack of any selectivity differences between UCB-3 and 3D Al-SSZ-70.

Figure 2C:
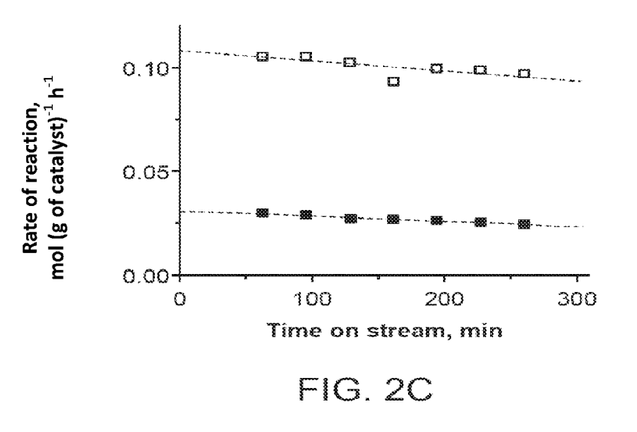
Figure 2D:
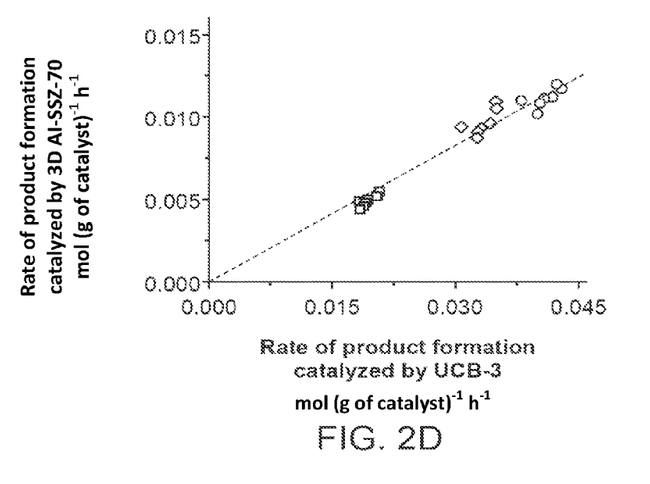
Figure 3:
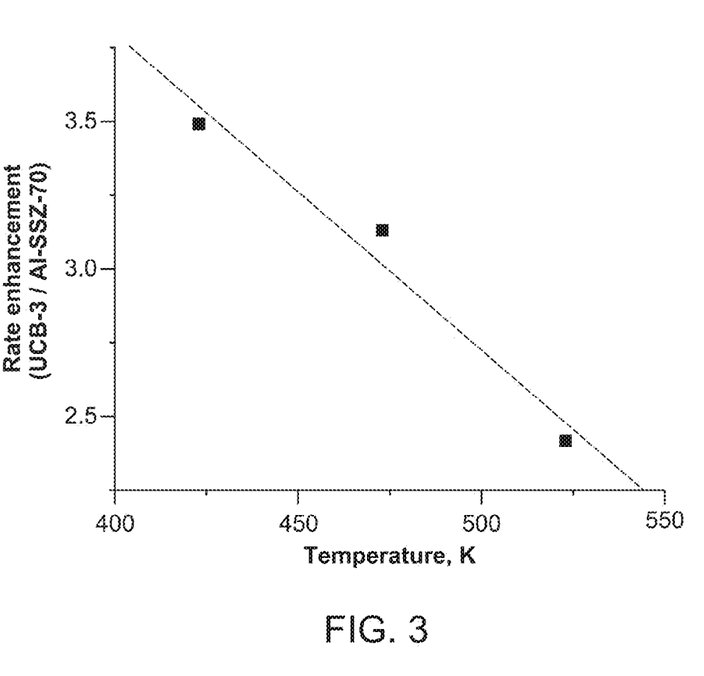
FIG. 3 depicts rate enhancement (reaction rate of UCB-3 divided by reaction rate of Al-SSZ-70) decreases as a function of temperature, which is expected as internal diffusion becomes less significant at increasing temperatures relative to reaction rate.
Figure 4A:
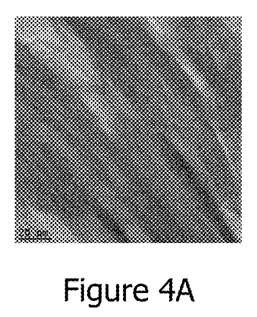
FIGS. 4A-4D are TEM images characterizing (4A) as-made Al-SSZ-70 precursor and (4B, 4C and 4D) UCB-3 delaminated zeolite. Both materials are uncalcined. The circles indicate the presence of shorter sheets that are evident in the UCB-3 images.
Figure 4B:
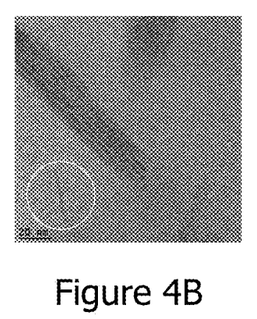
Figure 4C:
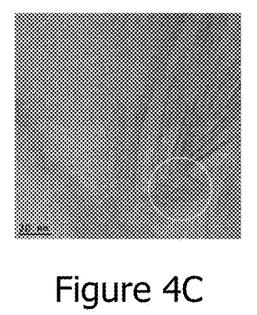
Figure 4D:
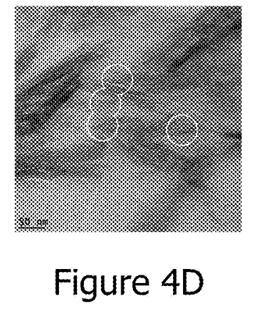

Upon decreasing reaction temperature to 423 K (150° C.) in FIG. 2C, calcined UCB-3 is 3.5-fold more active relative to Al-SSZ-70, while showing a similar selectivity profile for the various product isomers in FIG. 2D. FIG. 3 shows the overall trend at these reaction temperatures, and demonstrates an increasing relative-rate enhancement upon delamination as temperature decreases. If the only reason for the observed rate enhancement upon delamination was an increase in the density of external acid sites, as shown in FIG. 1A, the relative rate enhancement should be fixed and not change significantly with reaction temperature. Instead, the unequivocal increase in observed relative rate enhancement for UCB-3 in FIG. 3 indicates that an additional mechanism for rate enhancement upon delamination must exist, which is not captured entirely by FIG. 1A.

Figure 1B:
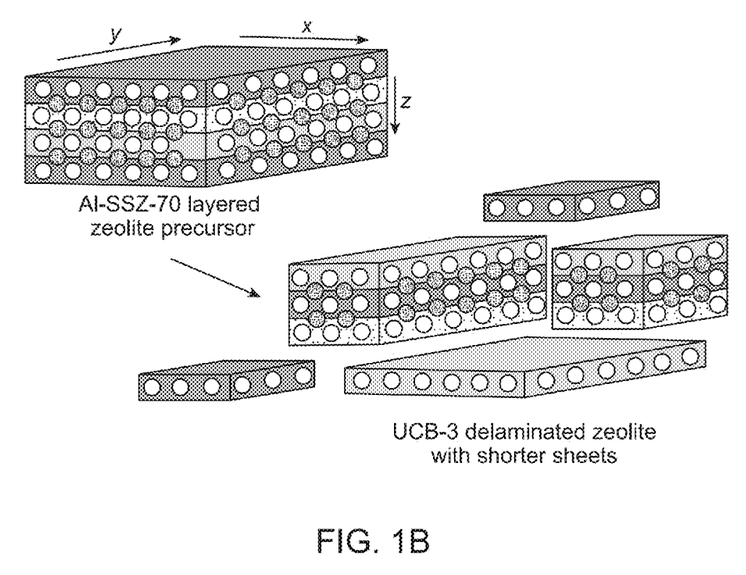

TEM micrographs in FIGS. 4A-4D compare the morphology of as-made Al-SSZ-70 and UCB-3. These data demonstrate long rectilinear sheets that break into smaller fragments upon delamination. Circles highlight fragmented sheets in as-made UCB-3, which are not observed in as-made Al-SSZ-70 in FIGS. 4B-4D. Such sheet breakage provides a heretofore unrecognized route by which delamination could enhance catalysis, by effectively providing a shorter diffusion path length to interior acid sites. This is schematically represented in FIG. 1B. Such a mechanism of enhancing catalysis via delamination implicitly assumes that internal acid sites are catalytic accessible and active.

The catalytic activity of UCB-3 was compared with an industrial catalyst, Al-MCM-22, both of which are summarized in Table 1 above. UCB-3 exhibited a 2-fold increase in catalytic activity, which is all the more impressive given the mass basis used for comparing activity in FIGS. 2A-2D and given the slightly higher Si/Al ratio of UCB-3 (i.e. when using an acid site rather than mass basis), the activity enhancement for UCB-3 over Al-MCM-22 is further enlarged by an additional 2-fold relative to values reported above. UCB-3 and Al-MCM-22 exhibited similar selectivities to m-, p-, and o-isopropyltoluenes at 523 K, as demonstrated by a cross-plot of their rates of formation in FIG. 2B. Therefore, UCB-3 can be considered a drop-in replacement for Al-MCM-22, because it maintains a stable selectivity profile with time-on-stream, which is similar to fresh Al-MCM-22, while exhibiting a greater catalytic activity per gram and per total acid sites.

The following examples are provided in order to further illustrate the present invention, and are not meant to be limiting.

EXPERIMENTAL

Materials and Sample Preparation

All reagents used in zeolite synthesis, delamination, and chemisorption were of reagent-grade quality and were used as received.

Characterization

Amine Chemisorption

Pyridine (Sigma Aldrich, spectroscopic grade) and collidine (Sigma Aldrich, 99% 2,4,6-trimethylpyridine) chemisorption experiments were performed by thermogravimetric analysis (TA Instruments TGA 2950). Approximately 30 mg of sample in the proton form was heated to 823 K in 100 mL/min of a dry $N_2$ flow, followed by a soak at this temperature for 3 h. After cooling to 423 K (150° C.), approximately 50 μL of pyridine was injected to the inlet line via syringe, and the system remained at 423 K (150° C.) for 3000 min.

Acridine chemisorption experiments were performed on a Varian Cary 400 UV-VIS spectrometer. The zeolite sample was heated for at least 4 h at 448 K to remove water from the sample and cooled down in a desiccator. Acridine (Sigma Aldrich, 97%) was recrystallized two times in ethanol and used to prepare a 500 μmol acridine/g hexane stock solution. 2 mL of the acridine stock solution was added to approximately 3.00 mg zeolite for titration. In these samples, these amounts of zeolite and acridine corresponded to a 1:3 ratio of potential acid sites to mol acridine in solution. The titrated solution was collected 1 h after the titration and passed through a 0.45 μm syringe filter. The difference of UV-vis absorbance of the stock solution and titrated solution was recorded and calculated by a UV-vis spectrometer. The decrease in UV-vis absorbance after titration was used to calculate the external acid sites. Each sample was characterized three times and the measurement error is less than 5%.

Elemental Analysis

Elemental analysis was performed at Galbraith Laboratories (Knoxville, Tenn.). Aluminum content was determined by Inductively Coupled Plasma-Atomic Emission Spectroscopy (ICP-AES). Silicon content was determined by Flame Atomic Absorption Spectrophotometry (FLAA).

Powder X-Ray Diffraction

Powder X-ray diffraction (XRD) patterns were collected on a Bruker D8 Advance diffractometer using a Cu Kα radiation.

$N_2$ Physisorption $N_2$ physisorption isotherms were measured on a Micromeritics ASAP2020 at 77 K. Prior to measurement, samples were evacuated at 623 K for 4 h.

Scanning Electron Microscopy (SEM)

The SEM images were acquired using a JEOL JSM-6700F instrument. In cases where delaminated UCB-3 and Al-SSZ-70 were prepared from different synthesis liners, SEM characterization was performed to ensure the same morphology at the layered zeolite precursor stage.

Transmission Electron Microscopy (TEM)

The TEM images were recorded on a JEOL Model JEM-2010 (200 kV) at the University of California, Davis.

Scanning Transmission Electron Microscopy (STEM)

The STEM images of the zeolites were acquired on a 200 kV FEI Tecnai instrument at the Pacific Northwest National Laboratory. The samples were gently crushed between glass slides and dry-loaded onto holey-carbon copper grids for both sets of experiments.

Solid-State Nuclear Magnetic Resonance (NMR) Measurements $^{29}Si$ solid-state MAS NMR spectra were measured using a Bruker Avance 500 MHz spectrometer with a wide bore 11.7 T magnet and employing a Bruker 4 mm MAS probe. The spectral frequencies were 500.23 MHz for the $^1H$ nucleus and 99.4 MHz for the $^{29}Si$ nucleus. $^{29}Si$ MAS NMR spectra were acquired after a 4 µs-90 degree pulse with application of a strong $^1H$ decoupling pulse. The spinning rate was 12 kHz, and the recycle delay time was 300 s. $^{29}Si$ CP MAS NMR spectra were collected at a sample spinning rate of 8 kHz, and the cross polarization contact time was 2.0 ms under the same radiofrequency pulse power (62.5 kHz±8 kHz). NMR shifts were reported in parts per million (ppm) when externally referenced to tetramethylsilane (TMS). One dimensional (1D) $^{27}Al$ MAS NMR spectra were also recorded on a Bruker DSX-500 spectrometer (130 MHz for $^{27}Al$) after a 0.5 µs single pulse (nutation angle<π/18) with application of a strong $^1H$ decoupling pulse, at a sample spinning rate of 14 kHz. An external reference for $^{27}Al$ shift was 1 M aqueous solution of $Al(NO_3)_3$.

Preparation of 1,3-Diisobutylimidazolium Hydroxide (SDA) Solution.

Synthesis of 1,3-diisobutylimidazolium bromide ($SDA^+$ $Br^-$) was performed according to conventional known methods. See, Corma, A. Chem. Rev., 1995, 95, 559-614. $SDA^+$ $Br^-$ was ion-exchanged to the hydroxide form by contacting with two equivalents of an ion-exchange resin (Bio-Rad, AG1-X8) in water at room temperature for 24 h.

Synthesis of Al-SSZ-70.

Synthesis of Al-SSZ-70 (Si/Al=40) was performed according to conventional methods described in Corma, id. Typically, 0.171 g of aluminum hydroxide (Reheis F-2000, 50-53 wt % $Al_2O_3$) was dissolved in a mixture of 8.89 g of 1 N sodium hydroxide aqueous solution (Sigma-Aldrich), 6.88 g of distilled water, and 35.6 g of 0.5 mmol/g of $SDA^+OH^-$ solution. To this mixture, 5.5 g of fumed silica (Sigma-Aldrich, particle size, 0.007 µm) and seed crystals (as-made Al-SSZ-70, 1% of $SiO_2$) were added. The gel composition was $SiO_2$:0.010$Al_2O_3$:0.050 $Na_2O$:0.20 SDA: 30 $H_2O$. After the gel was stirred at room temperature overnight, it was divided into four portions, and each gel was transferred to a 23-mL Parr reactor equipped with a Teflon liner. Each reactor was sealed and heated while tumbling at 60 rpm at 423 K (150° C.) for a period of 1-2 weeks. After cooling, the solid product was collected by centrifugation, washed thoroughly with distilled water, and dried at 353 K in a convection oven overnight. Calcination of Al-SSZ-70 was performed in an $O_2$/Ar flow at 823 K (550° C.) for 12 h. The product was determined by X-ray diffraction (XRD) to be SSZ-70.

Synthesis of UCB-3 Via Delamination of Al-SSZ-70.

Synthesis of UCB-3 (Si/Al=40) was performed according to the following procedure: A mixture of 0.50 g of as-made Al-SSZ-70, 0.55 g of cetyltrimethylammonium bromide (CTAB) (Sigma-Aldrich, ≥99.0%), 0.85 g of tetrabutylammonium fluoride trihydrate (TBAF) (Sigma-Aldrich, ≥97%), and 0.85 g of tetrabutylammonium chloride (TBACl) (Sigma-Aldrich, ≥97%) in 20 mL of DMF (Fischer Scientific) was placed in a screw-capped 50 mL PFA tube, and stirred using a magnetic stir bar at 373 K for 16 h in an oil bath. After cooling, the slurry was sonicated for 1 h in an ice bath, using a Branson digital sonifier 450 (Branson, USA) operating under pulse mode (1.0 s on and 0.1 s off). The sonicated slurry was filtered so as to separate a solid from a brown-colored filtrate. The solid was washed with DMF and then with ethanol thoroughly, and dried at 323 K (50° C.) overnight, yielding a white solid. Calcination of UCB-3 was performed in an $O_2$/Ar flow at 823 K for 12 h.

Figure 5:
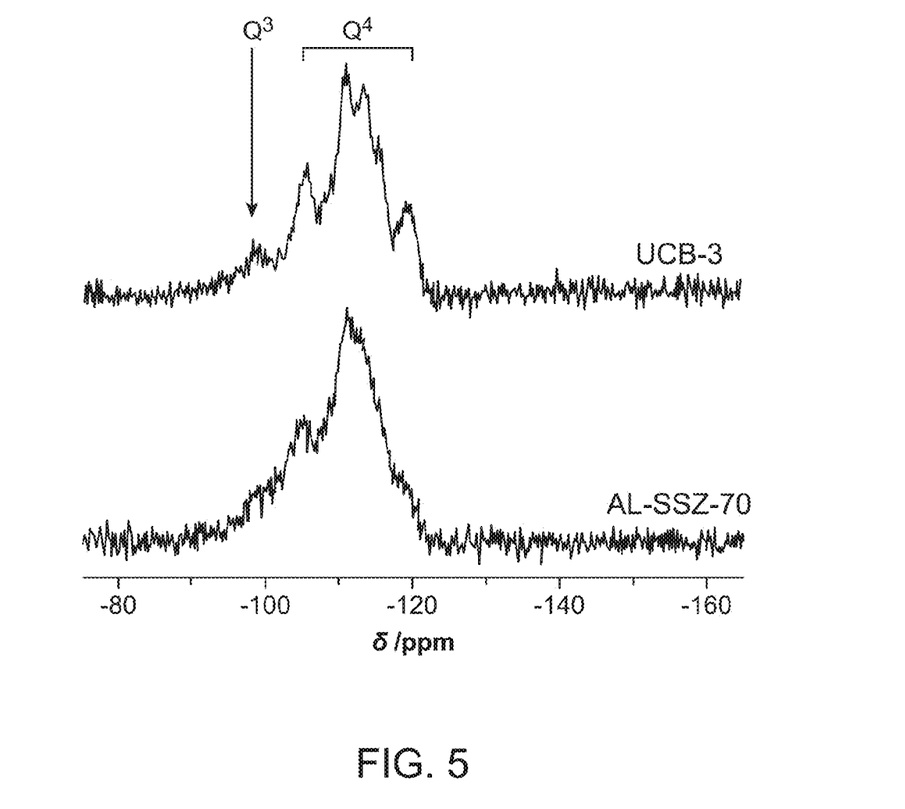
FIG. 5 shows $^{29}$Si MAS NMR spectra of calcined Al-SSZ-70 and calcined UCB-3.

$^{29}Si$ MAS NMR spectra characterizing the calcined Al-SSZ-70 and the calcined UCB-3 in FIG. 5 shows the complete lack of $Q^2$ resonance at approximately –90 ppm, which suggests a lack of amorphous silica on the zeolite framework within the actual materials used for catalysis here. This is a direct result of the mild delamination conditions. The spectra also show only slight differences between UCB-3 and Al-SSZ-70 in the $Q^3$ and $Q^4$ resonances in the range of –96.5 and –124.0 ppm. These data indicate that the crystallinity of UCB-3 is at least equal to that of Al-SSZ-70. These data are consistent with delamination of Al-SSZ-70 layers to form UCB-3 and with preserving the two-dimensional intralayer zeolite framework of UCB-3 intact because of the mild delamination conditions.

Ion-exchange of Al-SSZ-70 or UCB-3.

Calcined material was contacted with 0.2 M $NH_4NO_3$ aq. ($NH_4^+$/Al ratio>10) at 353 K (80° C.) for 1 h. This procedure is repeated four times, and the slurry was filtered. The resultant solid was dried at 353 K in a convection oven overnight. The ammonium—exchanged material was calcined to the H-form zeolite under the following conditions: under flowing dry air, the temperature was increased to 823 K (550° C.) at a rate of 1 K $min^{-1}$ and soaked at this temperature for 5 h.

Alkylation of Toluene with Propylene Catalysis

Catalytic reactions were carried out in a once-through packed-bed plug-flow reactor under the following conditions, with liquid toluene (Sigma-Aldrich, ≥99.9%) vaporized into a flowing gas stream: catalyst mass, 5-20 mg; temperature, 423-523 K (150-250° C.); pressure, 140 kPa; toluene liquid flow rate, 0.0596 mol $h^{-1}$; gas feed flow rate, 0.244 mol $h^{-1}$, as 0.214 mol $h^{-1}$ He (Praxair, 99.999%) and 0.0295 mol $h^{-1}$ 20% $C_3H_6$ (Praxair, 5% Ar with balance He). Each catalyst powder was diluted with particles of inert, nonporous α-Al$_2$O$_3$. The product gas stream was heated to 403 K (130° C.). Samples were periodically analyzed by gas chromatography.

Data were obtained using the same mass of either UCB-3 or Al-SSZ-70 under differential conversion conditions and at each temperature. Differential conversion conditions (i.e. relatively low conversion) were chosen because the rates of reaction are directly determined from the relationship of conversion as a function of space velocity, and because the contributions of secondary reactions to rates of product formation are minimized. Rates of formation and selectivities for isopropyltoluene isomers and 2,4-diisopropyltoluene were determined. Because of the low conversion conditions, trace product FID peak areas observed were nearly two-orders of magnitude lower and were, therefore, not quantified. Differential conversion conditions have been shown for low conversion (X≤0.2) alkylation of aromatics by MCM-22. Differential conversion conditions, used in all experiments, were achieved by changing the mass of the catalyst in the packed bed.

All patents and publications referenced herein are hereby incorporated by reference, in their entirety, to the extent not inconsistent with the present disclosure. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A method of alkylating an aromatic compound comprising contacting an aromatic compound and an alkylating agent in the presence of a UCB-3 catalyst under reaction conditions suitable for aromatic alkylation.
2. The method of claim 1, wherein the aromatic compound comprises benzene, toluene, or a mixture thereof.
3. The method of claim 1, wherein the aromatic compound comprises toluene.
4. The method of claim 1, wherein the alkylating agent comprises an alkane, olefin or an alcohol.
5. The method of claim 4, wherein the alkylating agent comprises an olefin.
6. The method of claim 5, wherein the olefin comprises ethylene or propylene.
7. The method of claim 5, wherein the olefin comprises propylene.
8. The method of claim 4, wherein the alkylating agent comprises an alcohol.
9. The method of claim 8, wherein the alcohol comprises methanol.
10. The method of claim 8, wherein the alcohol comprises isopropanol.
11. The method of claim 1, wherein the contacting is at a temperature in the range of 0° C. to 500° C.
12. The method of claim 11 wherein the contacting is at a temperature in the range of 150° C. to 250° C.
13. The method of claim 11, wherein the contacting is at a pressure in the range of 0.2 to 250 atm.
14. The method of claim 1, wherein the aromatic compound comprises benzene.
15. The method of claim 14, wherein the alkylating agent comprises ethylene, propylene, isopropanol or a mixture thereof.
16. The method of claim 14, wherein the alkylating agent comprises ethylene or propylene.

* * * * *